(12) United States Patent
Pasquino et al.

(10) Patent No.: US 11,272,971 B2
(45) Date of Patent: Mar. 15, 2022

(54) ELECTROMAGNETIC TISSUE ABLATION DEVICE

(71) Applicants: MYRA Medical Sàrl, Savigny (CH); GEM srl, Viareggio (IT)

(72) Inventors: Enrico Pasquino, Savigny (CH); Guido Bettoni, Erbusco (IT)

(73) Assignees: MYRA Medical Sàrl, Savigny (CH); GEM Srl, Viareggio (IT)

( * ) Notice: Subject to any disclaimer, the term of this patent is extended or adjusted under 35 U.S.C. 154(b) by 11 days.

(21) Appl. No.: 15/763,895

(22) PCT Filed: Sep. 30, 2016

(86) PCT No.: PCT/IB2016/055873
§ 371 (c)(1),
(2) Date: Mar. 28, 2018

(87) PCT Pub. No.: WO2017/056056
PCT Pub. Date: Apr. 6, 2017

(65) Prior Publication Data
US 2018/0280070 A1  Oct. 4, 2018

(51) Int. Cl.
*A61B 18/18* (2006.01)
*A61B 18/02* (2006.01)
(Continued)

(52) U.S. Cl.
CPC .......... *A61B 18/02* (2013.01); *A61B 18/1206* (2013.01); *A61B 18/1477* (2013.01); *A61B 18/1815* (2013.01); *A61B 18/24* (2013.01); *A61B 18/1492* (2013.01); *A61B 2017/00327* (2013.01); *A61B 2018/00017* (2013.01); *A61B 2018/00023* (2013.01); *A61B 2018/0044* (2013.01); *A61B 2018/00184* (2013.01);
(Continued)

(58) Field of Classification Search
None
See application file for complete search history.

(56) References Cited

U.S. PATENT DOCUMENTS 7,226,446 B1 * 6/2007 Mody ................ A61B 18/18
606/33
7,393,350 B2  7/2008 Maurice
(Continued)

FOREIGN PATENT DOCUMENTS

CN  103025262  4/2013
JP  2005504560  2/2005
(Continued)

OTHER PUBLICATIONS

International Search Report (ISR) of the International Search Authority (ISA) for PCT/IB2016/055873 dated Feb. 2, 2017.
(Continued)

*Primary Examiner* — Rex R Holmes
(74) *Attorney, Agent, or Firm* — Andre Roland S.A.; Nikolaus Schibli

(57) ABSTRACT

Electromagnetic (EM) tissue ablation device comprising an EM field generator unit, at least two coaxial elongated elements (i.e. an external one and an internal one) and a mechanism for varying the EM field, wherein said internal element is a part of said generator and said mechanism being adapted to vary the EM field for a specific tissue area.

15 Claims, 28 Drawing Sheets

| Cancer type | Frequently used ablation therapies |
|---|---|
| Breast | Radiation therapy, *Radiofrequency*, Cryoablation, Ultrasound, Microwave, Light |
| Colorectal | Radiation therapy, *Radiofrequency* |
| Kidney | Radiation therapy, *Radiofrequency*, Cryoablation, Microwave |
| Liver | Radiation therapy, *Radiofrequency*, Cryoablation, Microwave, Light |
| Lung | Radiation therapy, *Radiofrequency*, Microwave, Cryoablation, Light |
| Prostate | Radiation therapy, Cryoablation, Microwave, Light |
| Oesophagus | Radiation therapy, *Radiofrequency*, Laser |

(51) Int. Cl.
*A61B 18/24* (2006.01)
*A61B 18/14* (2006.01)
*A61B 18/12* (2006.01)
*A61B 18/00* (2006.01)
*A61B 17/00* (2006.01)
*A61B 18/20* (2006.01)

(52) U.S. Cl.
CPC ........... *A61B 2018/00345* (2013.01); *A61B 2018/00482* (2013.01); *A61B 2018/00517* (2013.01); *A61B 2018/00535* (2013.01); *A61B 2018/00559* (2013.01); *A61B 2018/00577* (2013.01); *A61B 2018/00714* (2013.01); *A61B 2018/00738* (2013.01); *A61B 2018/00755* (2013.01); *A61B 2018/00815* (2013.01); *A61B 2018/00898* (2013.01); *A61B 2018/00994* (2013.01); *A61B 2018/0212* (2013.01); *A61B 2018/0262* (2013.01); *A61B 2018/0293* (2013.01); *A61B 2018/1422* (2013.01); *A61B 2018/1823* (2013.01); *A61B 2018/1861* (2013.01); *A61B 2018/1869* (2013.01); *A61B 2018/2005* (2013.01)

(56) References Cited

U.S. PATENT DOCUMENTS

| | | |
|---|---|---|
| 7,422,586 B2 | 9/2008 | Morris et al. |
| 10,206,616 B2 | 2/2019 | Toth et al. |
| 2003/0073988 A1 | 4/2003 | Berube et al. |
| 2013/0116679 A1 | 5/2013 | Van Der Weide et al. |
| 2013/0310823 A1 | 11/2013 | Gelfand et al. |
| 2014/0066883 A1 | 3/2014 | Azamian et al. |
| 2015/0173831 A1 | 6/2015 | Rusin et al. |
| 2016/0008067 A1* | 1/2016 | Hadjicostis ........ A61B 18/1492 600/439 |
| 2016/0256678 A1* | 9/2016 | Vilims .................... A61N 1/08 |
| 2018/0036060 A1* | 2/2018 | Wegrzyn, III ....... A61B 18/082 |

FOREIGN PATENT DOCUMENTS

| | | |
|---|---|---|
| JP | 2008513154 | 5/2008 |
| JP | 2015521495 | 7/2015 |

OTHER PUBLICATIONS

Written Opinion (WO) of the International Search Authority (ISA) for PCT/IB2016/055873 dated Feb. 2, 2017.
Chinese Office Action dated May 20, 2020 for Application N° CN 201680067602.6—EN translation.
Japanese Office Action dated Sep. 8, 2020 for Application JP 2018-536353—EN translation.

* cited by examiner

| Cancer type | Frequently used ablation therapies |
|---|---|
| Breast | Radiation therapy, *Radiofrequency*, Cryoablation, Ultrasound, Microwave, Light |
| Colorectal | Radiation therapy, *Radiofrequency* |
| Kidney | Radiation therapy, *Radiofrequency*, Cryoablation, Microwave |
| Liver | Radiation therapy, *Radiofrequency*, Cryoablation, Microwave, Light |
| Lung | Radiation therapy, *Radiofrequency*, Microwave, Cryoablation, Light |
| Prostate | Radiation therapy, Cryoablation, Microwave, Light |
| Oesophagus | Radiation therapy, *Radiofrequency*, Laser |

FIG. 1

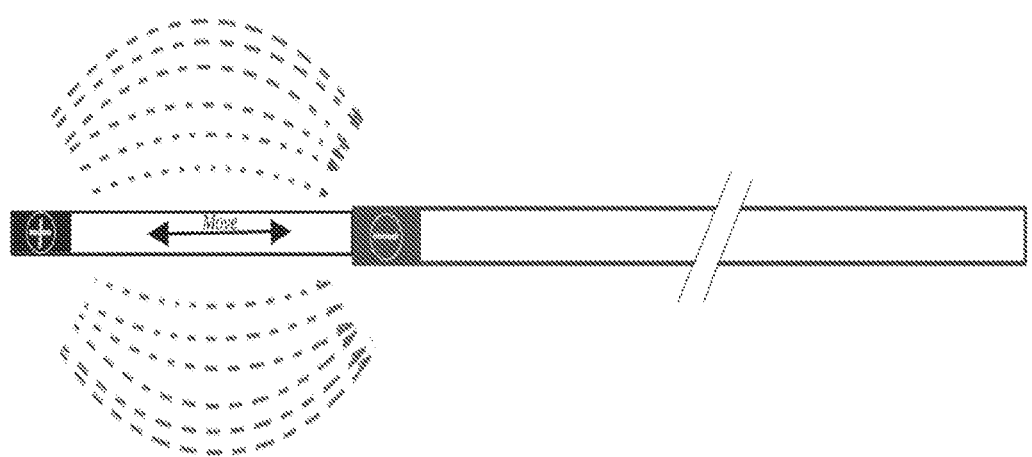

FIG. 2

ELECTROMAGNETIC TISSUE ABLATION DEVICE

CROSS REFERENCE TO RELATED APPLICATIONS

The present application is a U.S. national stage application of International Patent Application PCT/IB2016/055873 that was filed on Sep. 30, 2016 designating the United States, and claims foreign priority to International patent application PCT/IB2015/057490 that was filed on Sep. 30, 2015, the contents of both documents being herewith incorporated by reference in their entirety.

FIELD OF INVENTION

The present invention relates to tissue ablation and more precisely to electromagnetic tissue ablation.

TERMS AND DEFINITIONS

In the present document the expression "electromagnetic field" has to be understood as a combination of an electric field and a magnetic field. It covers any range of the electromagnetic (EM) spectrum, in particular the X-ray, UV, visible, infrared, microwave and radio.

This expression also includes an electric field alone (i.e. absence of magnetic field) and a magnetic field alone (i.e. absence of electric field).

The expression "electromagnetic tissue ablation device" has therefore to be understood as a tissue ablation device wherein ablation is generated by an electromagnetic field.

STATE OF THE ART

Electromagnetic tissue ablation, in particular RF, microwave or tissue laser ablation is a common surgical procedure.

RF tissue ablation treatment is nowadays relatively advanced in cardiology field (atrial fibrillation) and pain therapy but less in other medical areas such as oncology. This is essentially due to the fact that the devices used to deliver the energy source are disposable.

RF has two main uses for the treatment of tissues:
1) the ablative RF in cardiovascular, oncology, orthopedic, gynecology, gastroesophageal and intestinal endoscopy
2) the pulsed RF finds in epidural endoscopy.

The RF treatment of tumors in various organs (liver, prostate, thyroid, kidney, lung, etc.), besides radiation therapy, is largely used and clinically quite effective. The business forecasts estimate that it expected to become the preferred choice of treatment in 60% to 70% of the oncologic cases in the next 10 years (FIG. 1).

Another source of energy most frequently used in tissue ablation, which is not based on electromagnetic fields, is cryotherapy. It represents the treatment of choice in 5% of the cancer cases and in a certain type of tumors, such as the kidney and prostate tumors, is reaching 80% thanks to its efficacy. The counter side of the cryoablation is the cost that in some cases can become a limiting factor.

RF tissue ablation is carried out using a generator of RF and a disposable delivery device, usually a needle or a catheter used to deliver the RF energy to the tissues.

The RF treatment efficacy essentially depends on the amount of energy delivered and the procedural time but also on the following factors:

a. The location, orientation and intensity of the electric field generated by the RF;

b. The cooling of the delivery device. A part of the energy generated for the treatment is transformed into heat, which may lead to an important and sometimes dangerous increase of temperature of the surrounding tissues. The heating around the electrodes may cause a carbonization of the tissue with excessive damages to the tissues, increase of the electric impedance and a reduction of the treatment efficacy;

c. The steerability of the delivery device, in particular in tissue ablation treatments based on endoluminal access.

GENERAL DESCRIPTION OF THE INVENTION

One object of the invention is to provide a modulation of the treatment area.

Another object is to have an efficient cooling system.

Another object is to use cryoablation in combination with electromagnetic ablation.

Another object is to provide a steerability system for a catheter-based delivery device that allows to come closer to the treatment area, especially with endoluminal access, increasing the procedure efficacy.

Another object is the creation of a multipurpose delivery device suitable to be used in different medical fields with a needle or catheter-base shape with hybrid function shifting between two energy sources in multimode tasking.

Another object is to have a computer-based procedural control increasing the safety control of the tissue ablation conditions:

a. local tissue temperature control;

b. treatment duration;

c. electric impedance;

d. the dimension of the tissue's treated volume;

e. delivery device serial number recognition to impede re-use;

f. cooling conditions and cryoablation parameters' control in case of use;

g. alarm in case reaching critical temperature;

h. alarm against accidental retrieve of the delivery device during the procedure when needle electrodes are open or catheter is steered.

Another object is to have a support system, for the handle of the delivery device, equipped with multi-axial micrometric positioning control in order to precisely target the treatment area avoiding accidental misplacing of the delivery device and long-term holding-up of the device by the operator during the procedure.

Another object is to monitor the essential procedural parameters through a mini-screen mounted on the support system.

The present invention provides several advantages with respect to the state of the art.

In its broadest scope it relates an electromagnetic (EM) tissue ablation device comprising an EM field generator unit, at least two coaxial elongated elements (i.e. an external one and an internal one) and a mechanism for varying the EM field, wherein said internal element is a part of said generator and said mechanism being adapted to vary the EM field for a specific tissue area.

Varying the EM field area makes it possible to modulate the treatment area. The EM field intensity may be constant or variable but in any case the EM field has to be variable for a specific tissue area.

More than two coaxial electrodes may be used.

In a preferred embodiment the electrodes are movable relative to one another. With such a configuration the relative movement between the electrodes results in a variation of the electrical field.

Advantageously the device according to the invention also includes a gas-based cooling system which, for instance, may be made of several tubes which are located within the external electrode. In this case the diameter of the external electrode is preferably of less than 2 mm.

In another embodiment the device according to the invention has a cooling system that is adapted to be used as a cryoablation system, taken as such or in combination with said EM system.

The device according to the invention is not limited to a specific shape, materials or dimensions. The elongated elements and (if present) the cooling system may be located within and/or around a catheter. In that case the device may advantageously comprise a steering unit which, according to one embodiment, is based on a nut body guided by four ovoidal pins rotating over two semi-screws.

The catheter based version is preferably able to support intra-parenchymal or endoluminal tissue ablation procedures.

In another embodiment the electrodes are electrically connected to the power source by means of conductive polymers loaded with carbon nanotubes, said polymers being used for providing an electrical current to said electrodes.

The coaxial configuration of the elongated elements allows not only the control of the EM field but also the surface of tissue exposed to cryoablation. Furthermore, the use of cryoablation reduces the risk of cancerous cells dissemination during the retraction of the ablation device.

DETAILED DESCRIPTION OF THE INVENTION

The invention will be better understood in the present chapter which includes some examples, with or without figures.

BRIEF DESCRIPTION OF THE FIGURES

FIG. 1: Summary of the frequently used ablation therapies

FIG. 2: Example of a multipolar ablation device according to the invention

NUMERICAL REFERENCES USED IN THE FIGURES

Example A (FIGS. 6 to 9)

Figure 3:
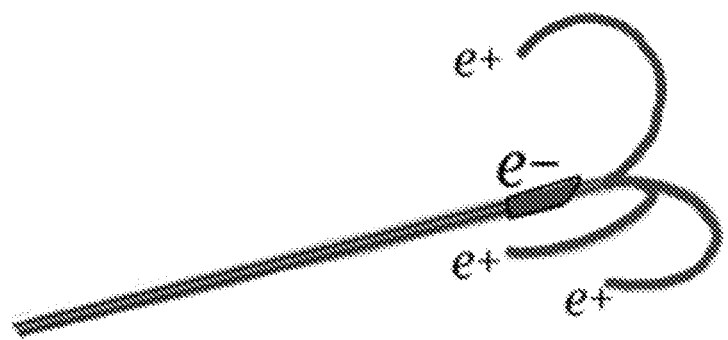
FIG. 3: Example of a multipolar anodic configuration according to the invention

1. Return cooling fluid pipe with thermistor sensor cables inside
2. Active needle and anode
3. Lumen to return cooling fluid
4. Lumen to send cooling fluid
5. Multi-sector profile with electrical insulation
6. Metal pipe (cathode)
7. Metal needle (cathode) to puncture tissue
8. Polymeric covering used to partial cathode effect in the proximal part of the system
9. 9a and 9b: Thermistor sensor cables
10. Thermistor sensor head
11. Closing needle material Example B (FIGS. 10 to 13)

12. Electrode anode shaft
13. Inflow cooling fluid pipe
14. Outflow cooling fluid lumen
15. Inflow cooling fluid lumen
16. Thermistor sensor tip
17. Metal pipe containing the thermistor sensor
18. Metal needle cathode used to perforate tissues
19. Polymeric covering used to reduce the cathode effect
20. 20a and 20b thermistor sensors' cables (used to monitor temperature)
21. 21a thermistor sensor head on cathode and thermistor 21b on anode
22. Closing needle material
23. Multi-lumen polymeric isolating pipe
24. 24a and 24b connection electrode cables (anode)

Example C (FIGS. 14 to 17)

25. Proximal electrodes (anode)
26. Multi-lumen shaft with telescopic function. Electrode holder for cathode, temperature control and cooling.
27. Outflow cooling fluid
28. Inflow cooling fluid
29. Bypass area of cooling fluid
30. Distal electrode (cathode)
31. Cathode conductive cable
32. Thermistors cables 32a and 32b for distal portion (32a and 32b also for proximal portion if needed)
33. Thermistor tip
34. Anode conductive cables 34a, 34b, 34c for anodes 25a, 25b, 25c
35. Multi-lumen shaft catheter to manage anode proximal electrodes Example D (FIGS. 18 to 21)

36. Proximal anode electrodes
37. Multi-lumen shaft with telescopic function. Cathode electrode holder, temperature control and cooling.
38. Outflow cooling fluid lumen
39. Inflow cooling fluid lumen
40. Cooling fluid bypass area
41. Distal cathode electrode 42. Cathode conductive cable
43. Thermistors cables 43a and 43b for distal portion (43a and 43b also for proximal portion if needed)
44. Thermistor tip
45. Anode conductive cables 45a, 45b, 45c for anodes 36a, 36b, 36c
46. Multi-lumen shaft catheter used to manage anode proximal electrode Example E (FIGS. 22 to 28)

Figure 29:
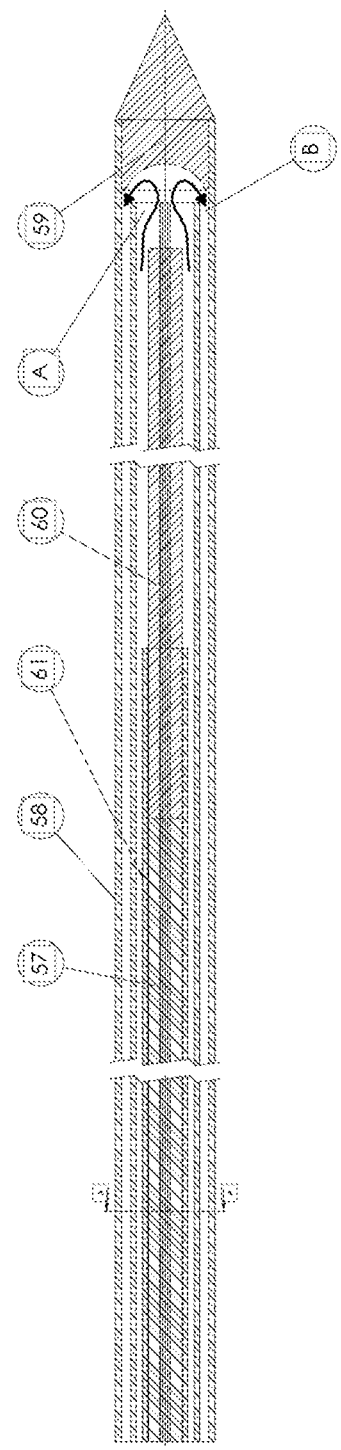
FIGS. 29 to 33: Example of a laser ablation device according to the invention
Figure 30:
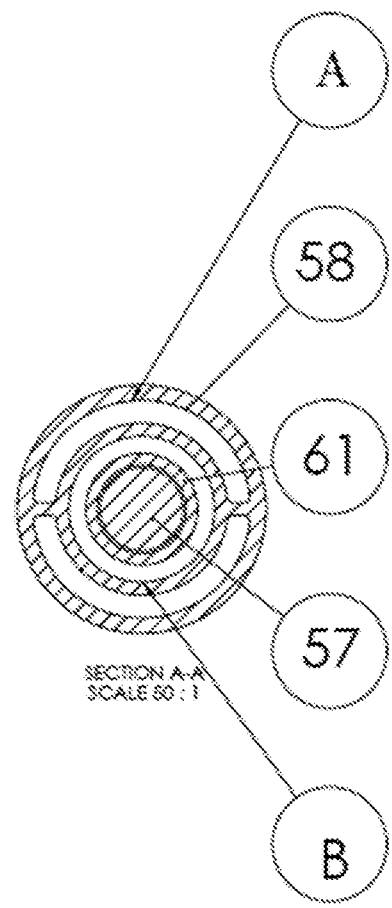
Figure 31:
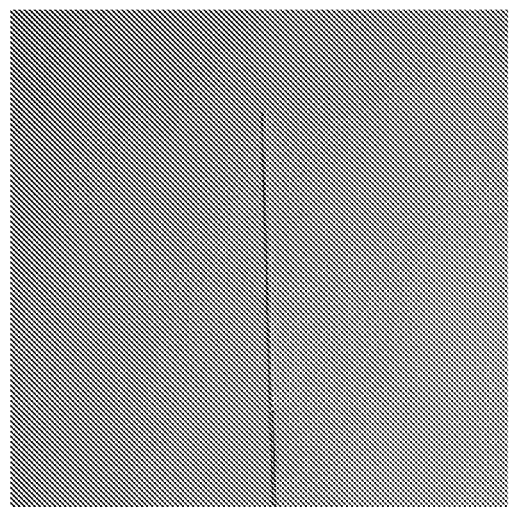
Figure 32:
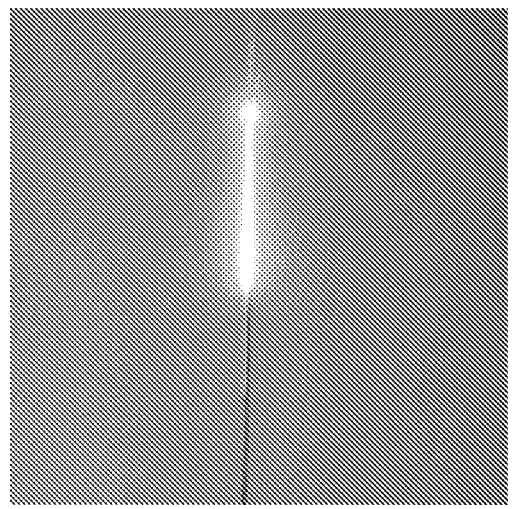
Figure 33:
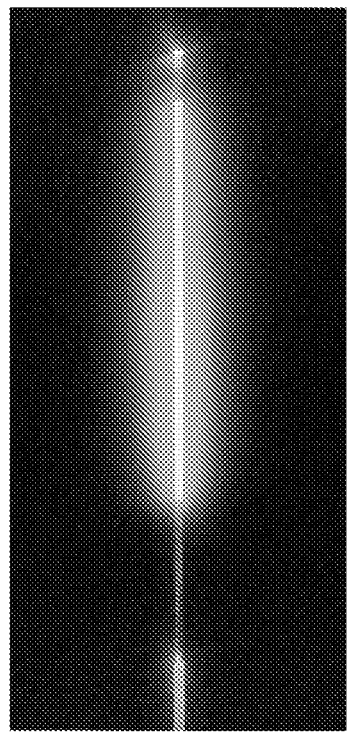

47. Electrode
48. Conductive element
49. Insulating element
50. Metallic sleeve
51. External shield
52. First coaxial lumen
53. Second coaxial lumen
54. Tip
55. Multilumen catheter
56. Antenna Example F (FIGS. 29 and 30)

57. Optical fiber
58. Multilumen structure
59. Tip
60. Exposed portion
61. Moving tube In a first preferred embodiment the invention is based on a multipolar, e.g. bipolar, RF delivery device. The device may be a needle, a catheter or any other suitable element where the electrodes are electrically isolated and coaxial so that it is possible to modulate the amplitude of the treatment area, as shown on FIG. 2.

In this illustrated example the RF delivery device consists in two coaxial tubes in which the cathode is placed at the extremity of the outer tube while the anode is placed proximally at the extremity of the inner tube. The inner wall of the outer tube, carrying on the cathode, is electrically isolated in order to avoid a shortcut with the anode. The relative movement of the two tubes defines the amplitude of the electrical field therefore the extension and the depth of the tissue ablation treatment. This approach avoids the positioning of an external anodic plate in contact with the patient's skin, which causes a less precise control of the resulting electric field.

In this example the anode is a single tip but in an alternative configuration, applicable to a needle-based solution, it can include a multipolar anodic configuration as represented in FIG. 3.

Figure 4:
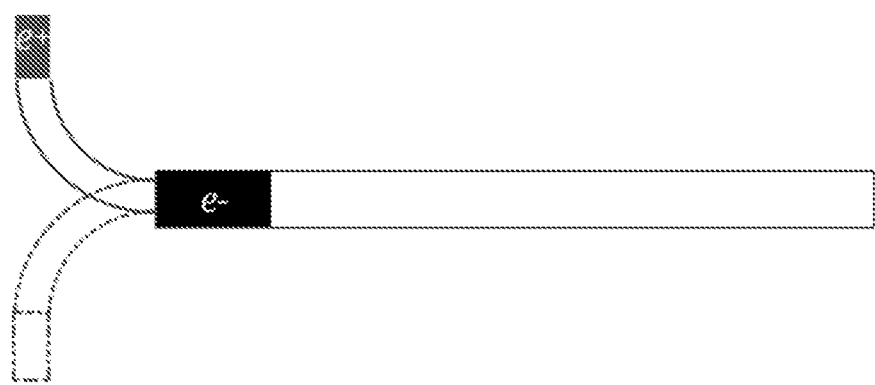
FIG. 4: Example of a steering of a catheter according to the invention

In another configuration applicable to a catheter-based solution the same tissue ablation effect can be obtained with a steering of the catheter as presented in FIG. 4.

The materials used to realize the needles are preferably metallic alloy tubes realized with conventional technologies or in alternative by a new technology based on a multi-lumen extrusion of metallic powder that is thereafter synthesized.

On the other side the catheter-based delivery device can take advantage of all well-known polymer extrusion technologies but adding an important feature represented by the conductivity. The electrical conductivity of polymeric catheters can be obtained extruding the polymer matrix adding carbon nanotubes.

In addition to the multipolar features the device may be equipped with a gas-based cooling system that can also act as a cryotherapy treatment allowing a hybrid procedure.

Figure 5:
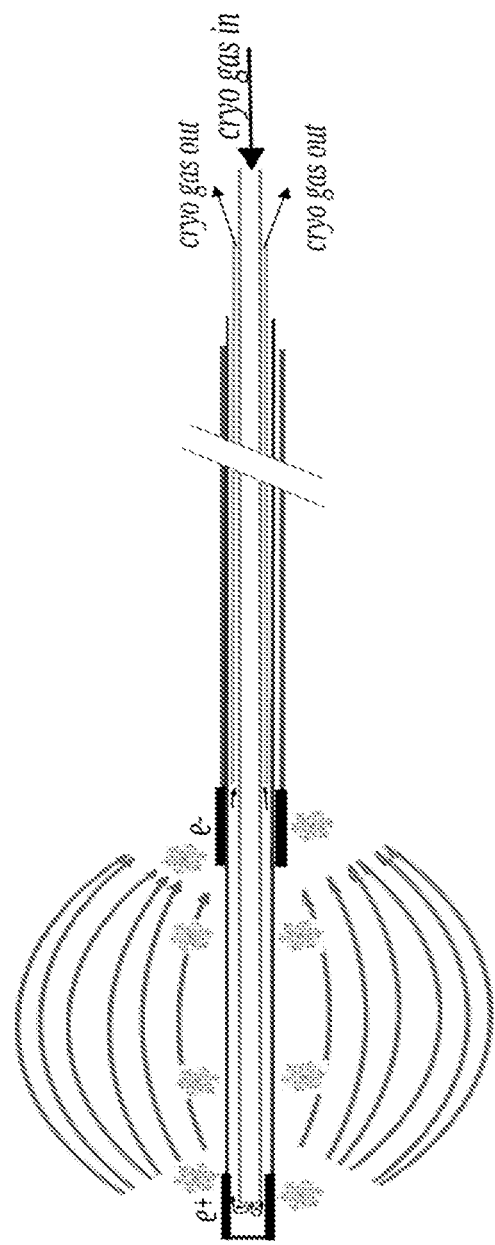
FIG. 5: Example of a device according to the invention that includes a cryo/cooling system
Figure 6:
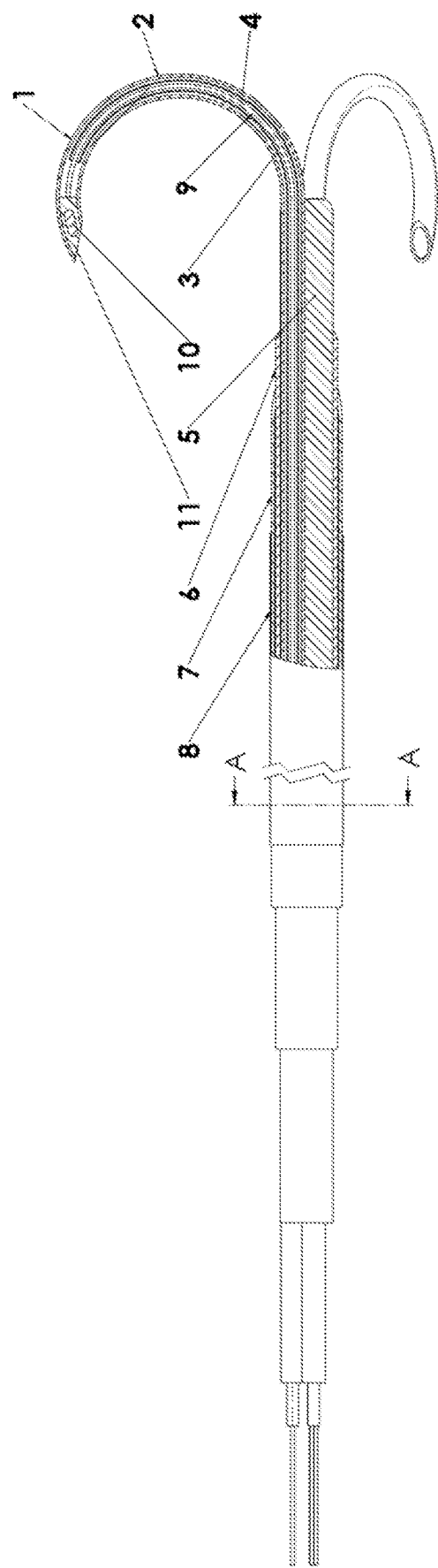
FIGS. 6 to 9: Example of a RF ablation device according to the invention
Figure 7:
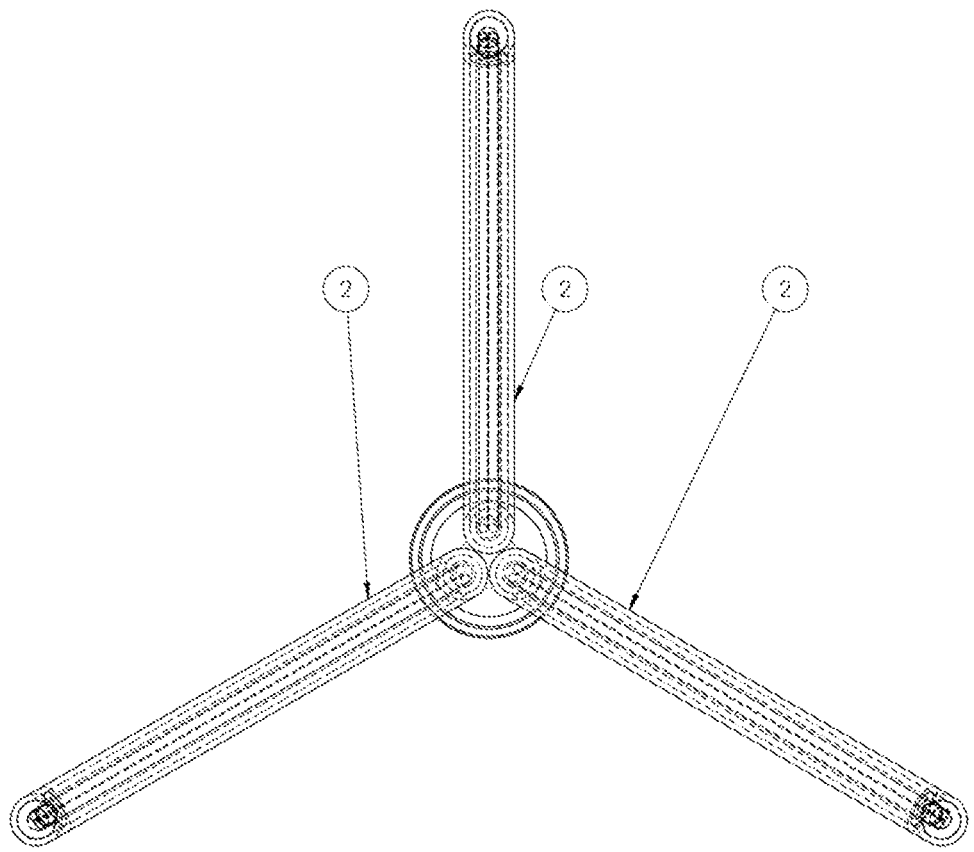
Figure 8:
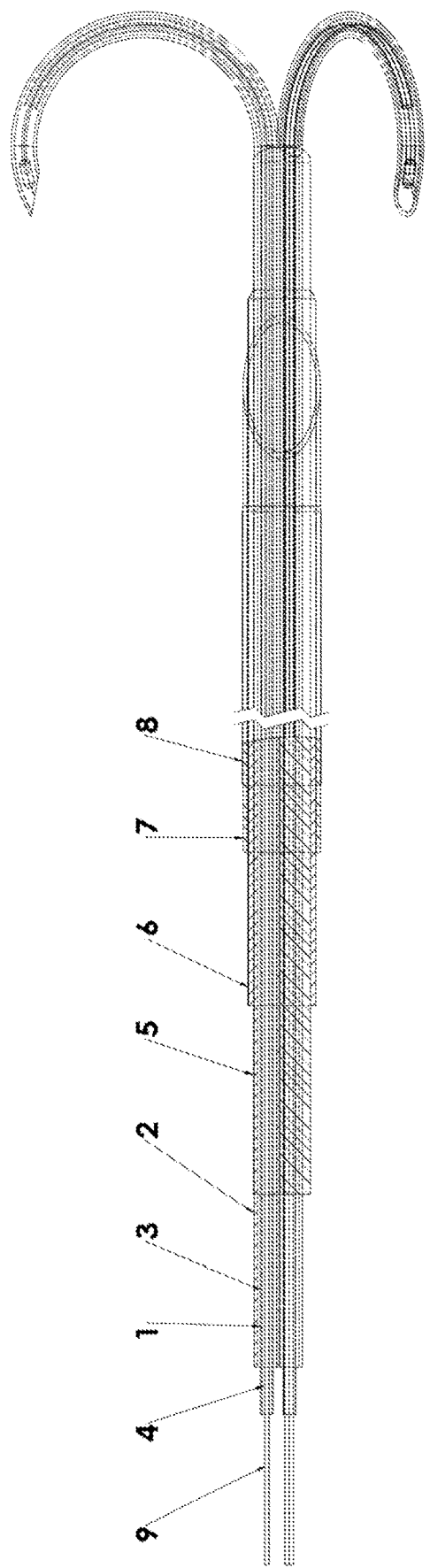
Figure 9:
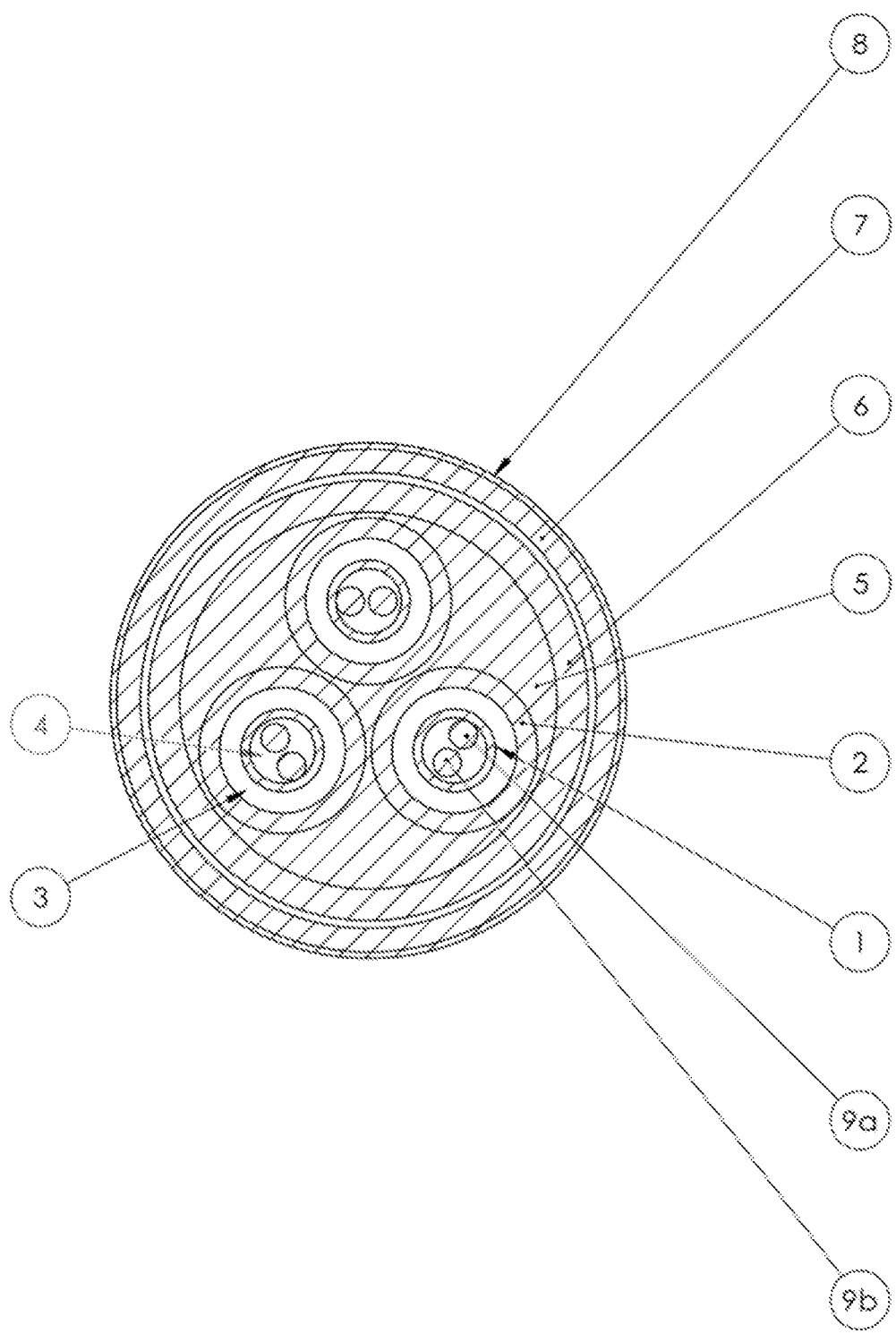
Figure 10:
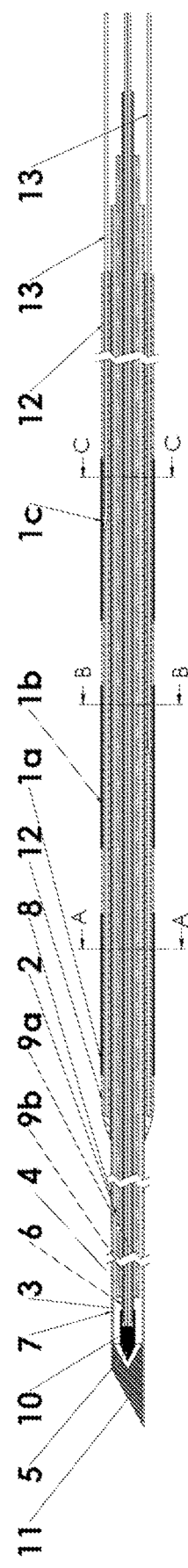
FIGS. 10 to 13: Another example of a RF ablation device according to the invention
Figure 11:
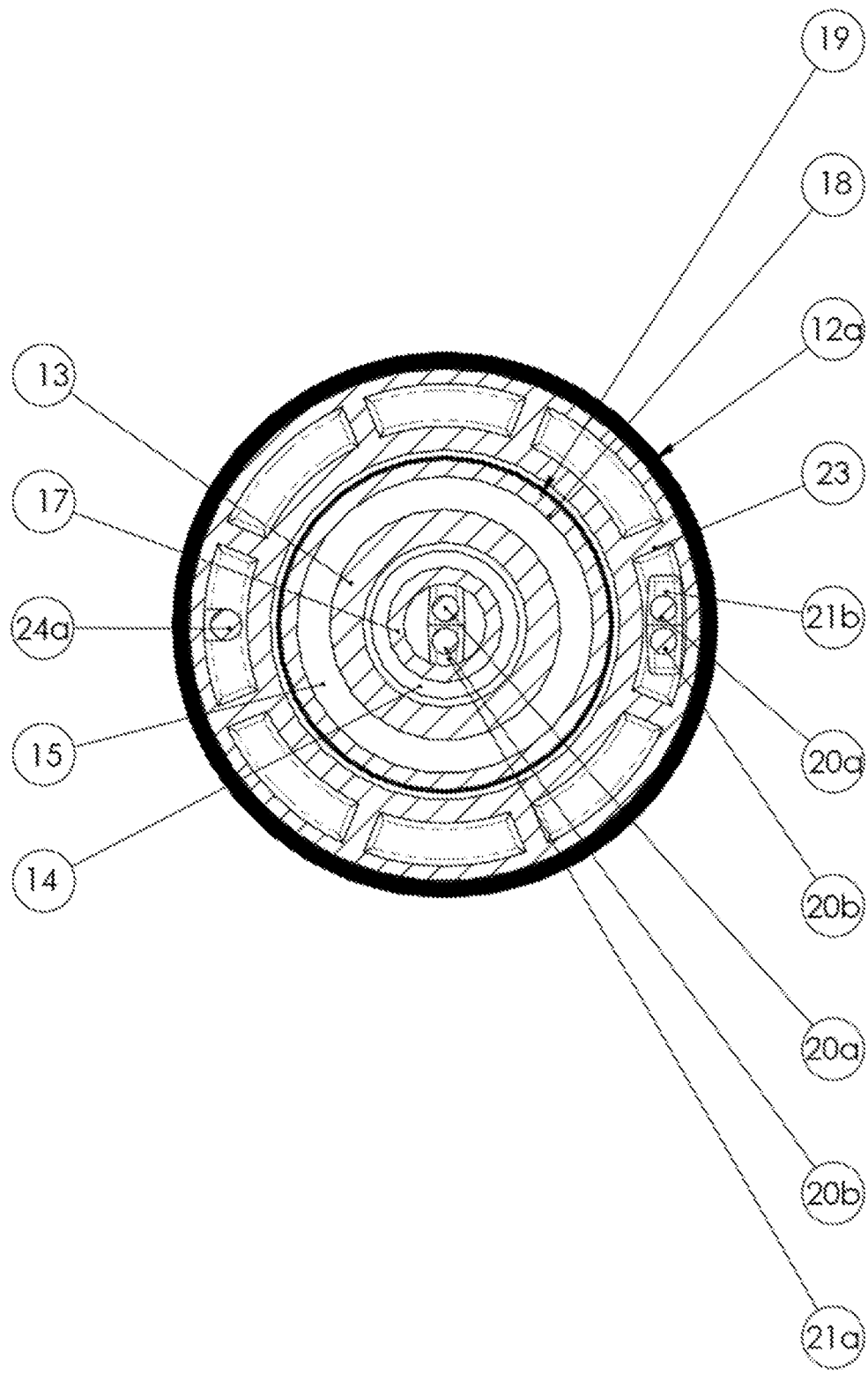
Figure 12:
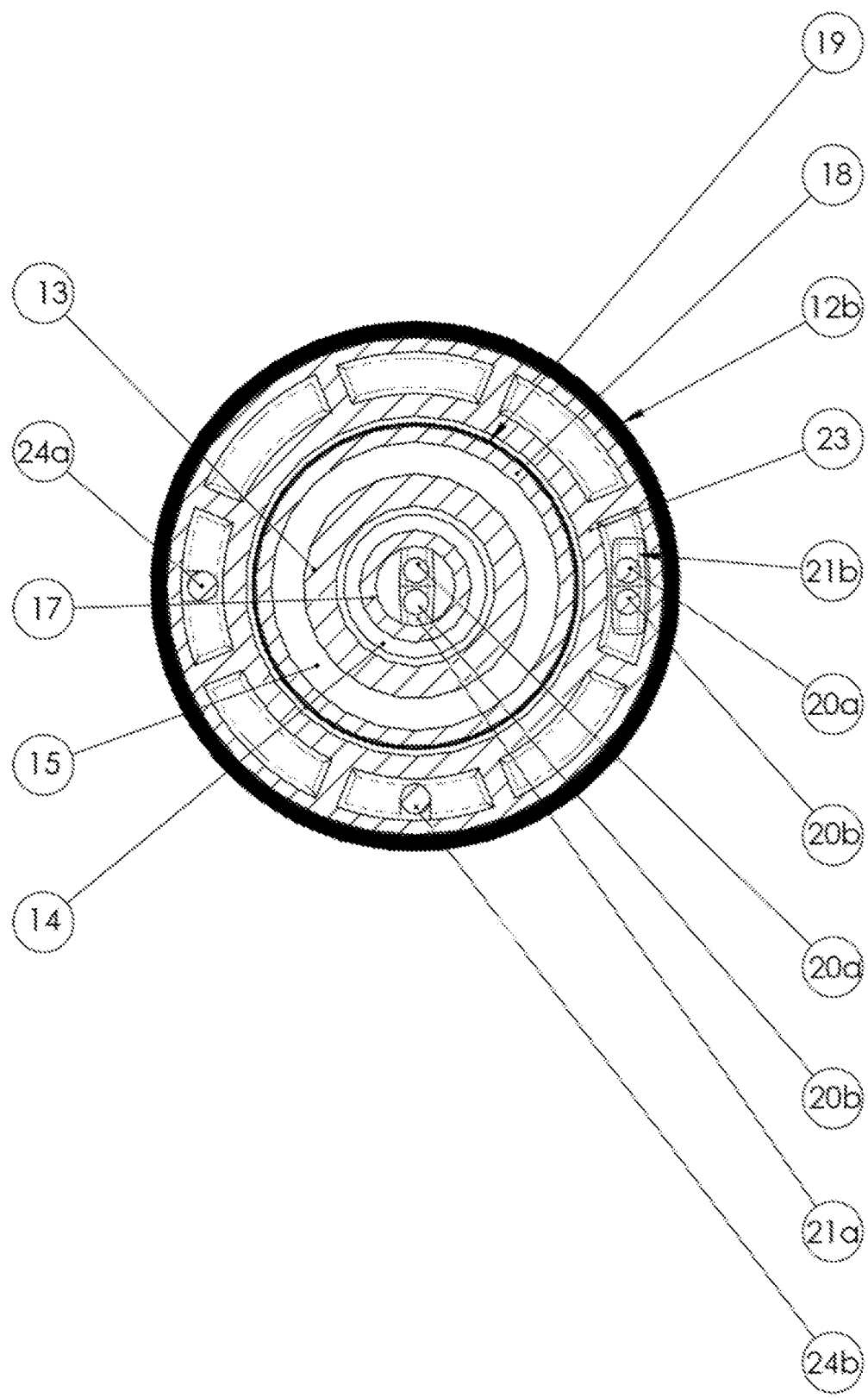
Figure 13:
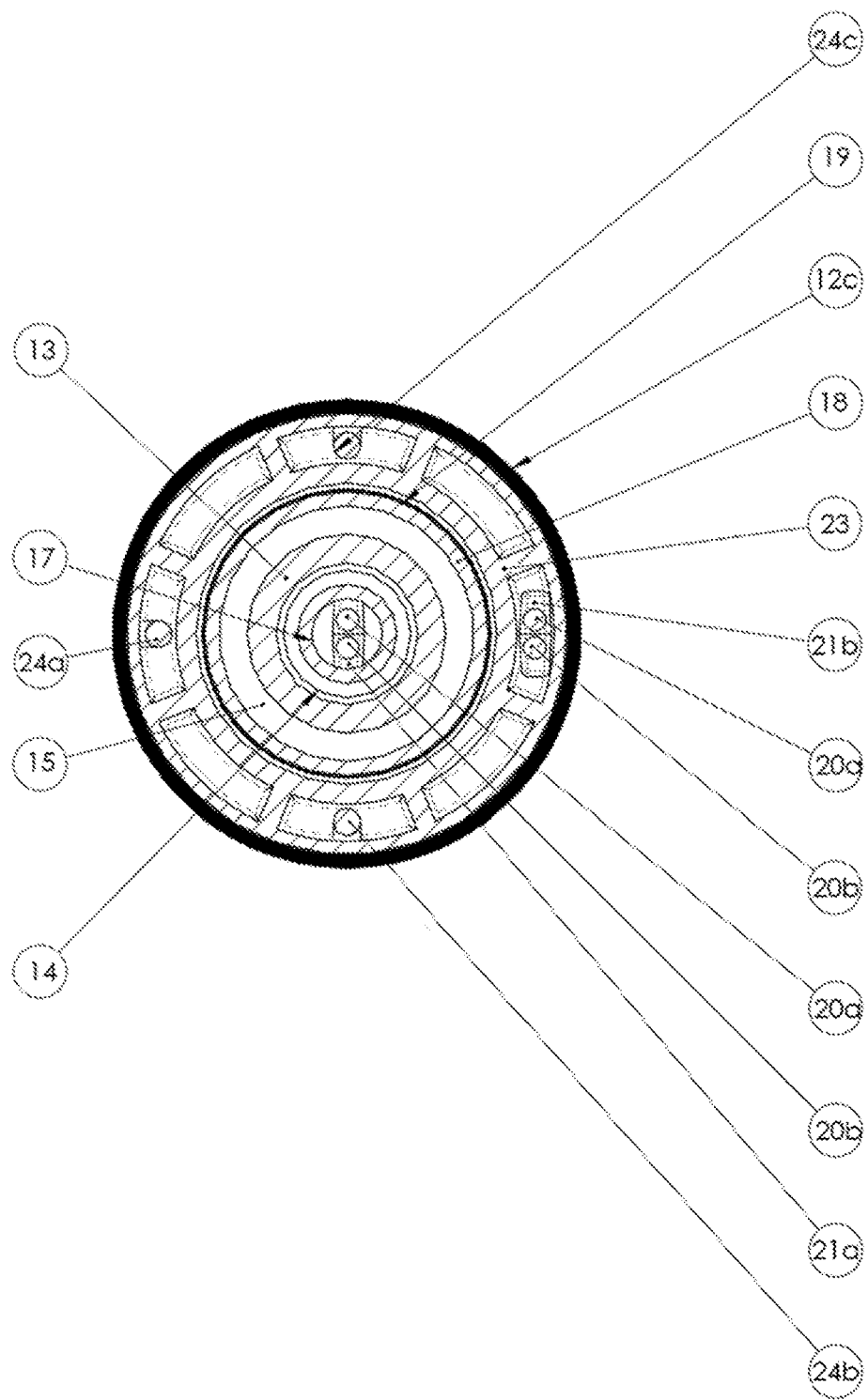
Figure 14:
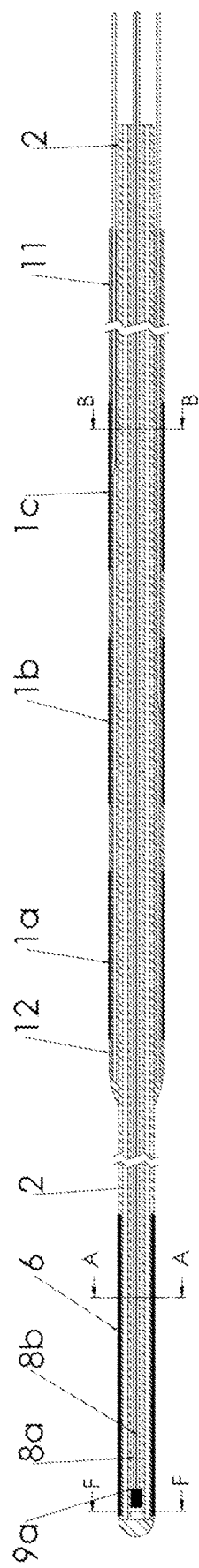
FIGS. 14 to 17: Another example of a RF ablation device according to the invention
Figure 15:
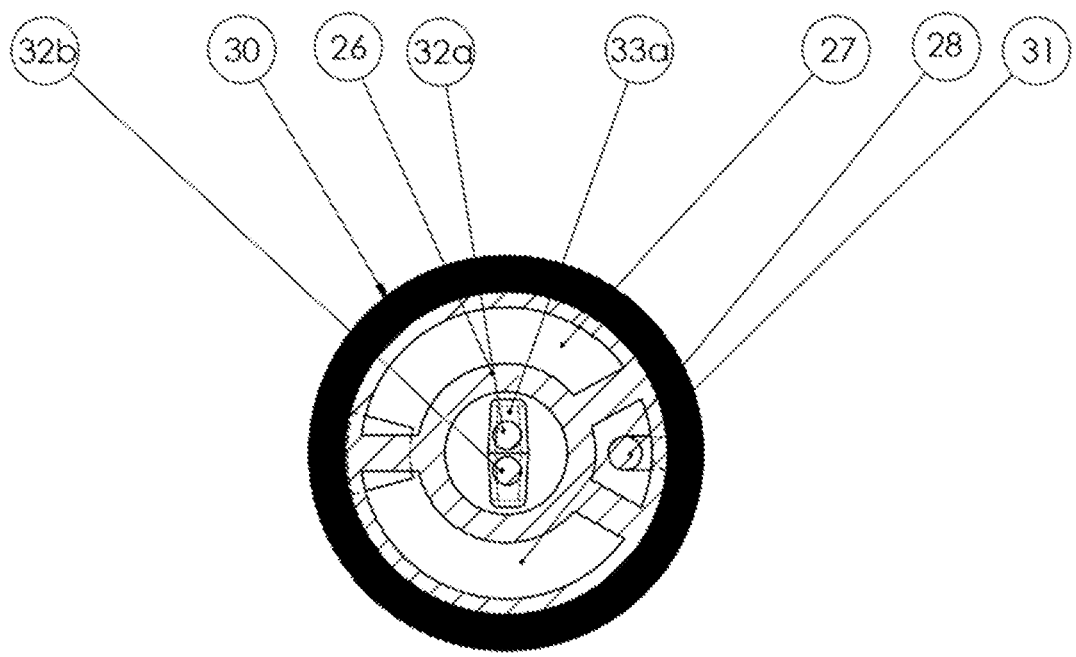
Figure 16:
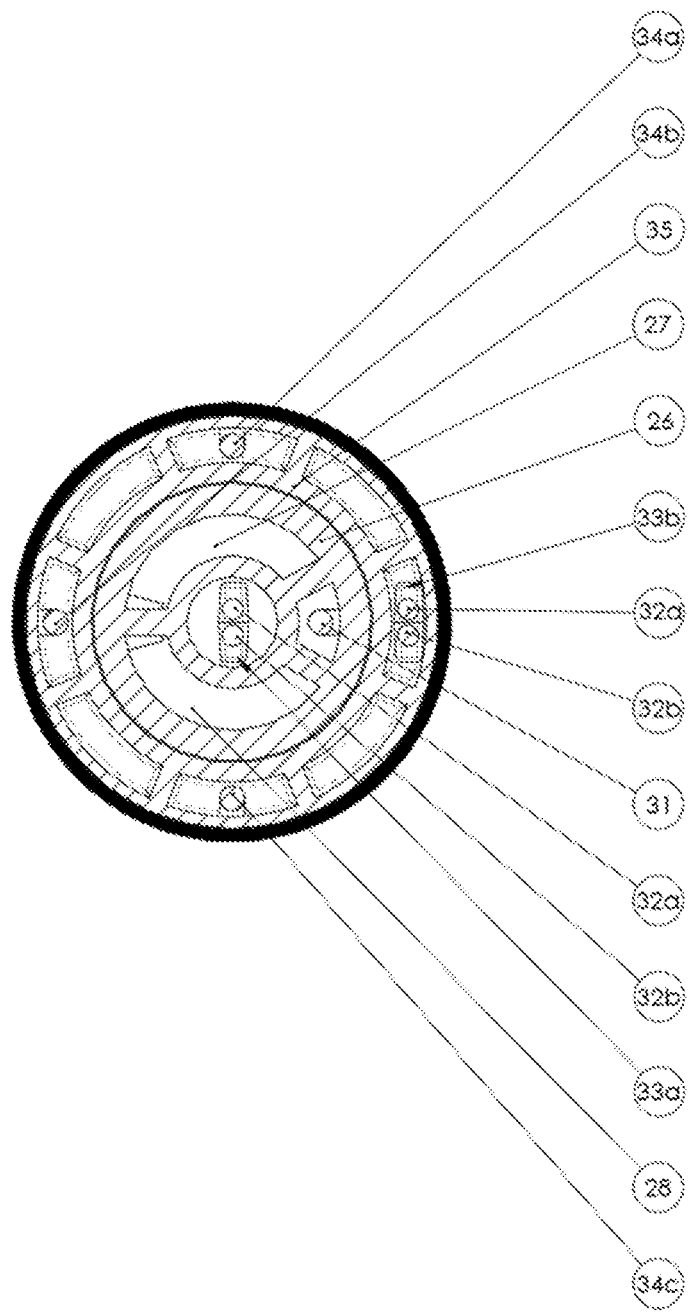
Figure 17:
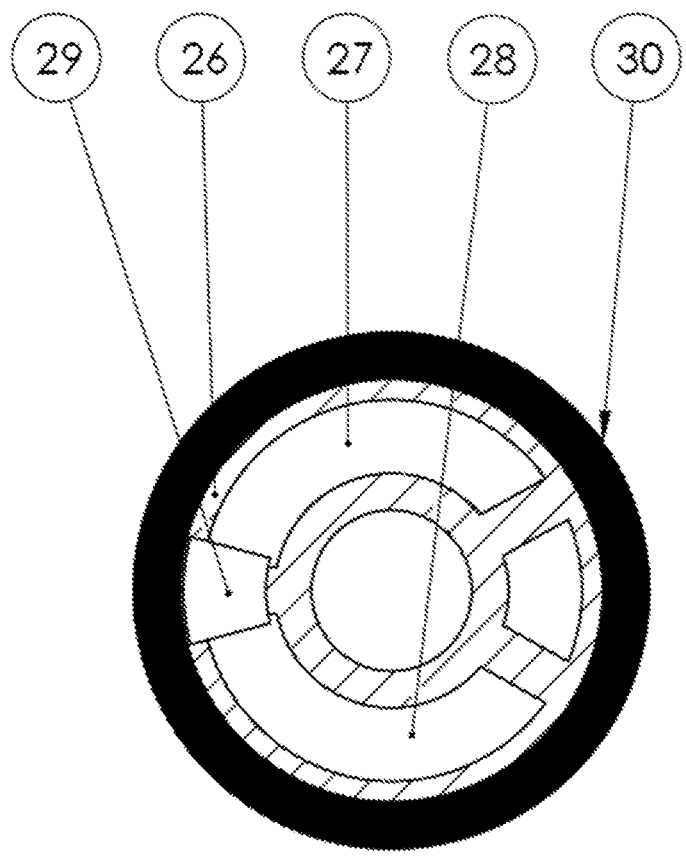
Figure 18:
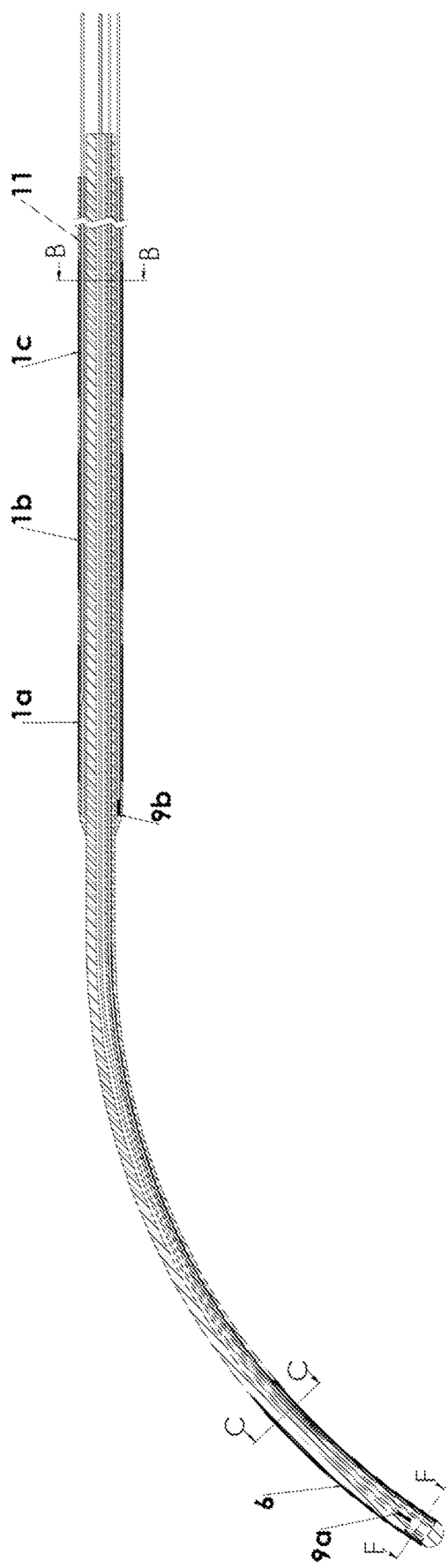
FIGS. 18 to 21: Another example of a RF ablation device according to the invention
Figure 19:
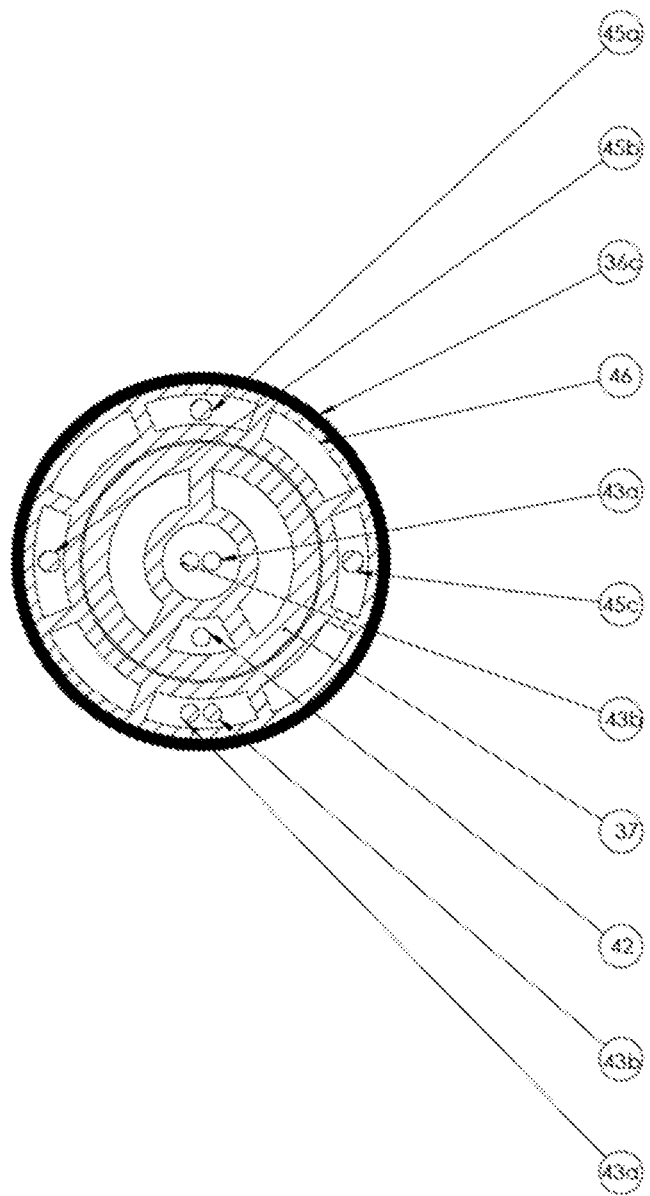
Figure 20:
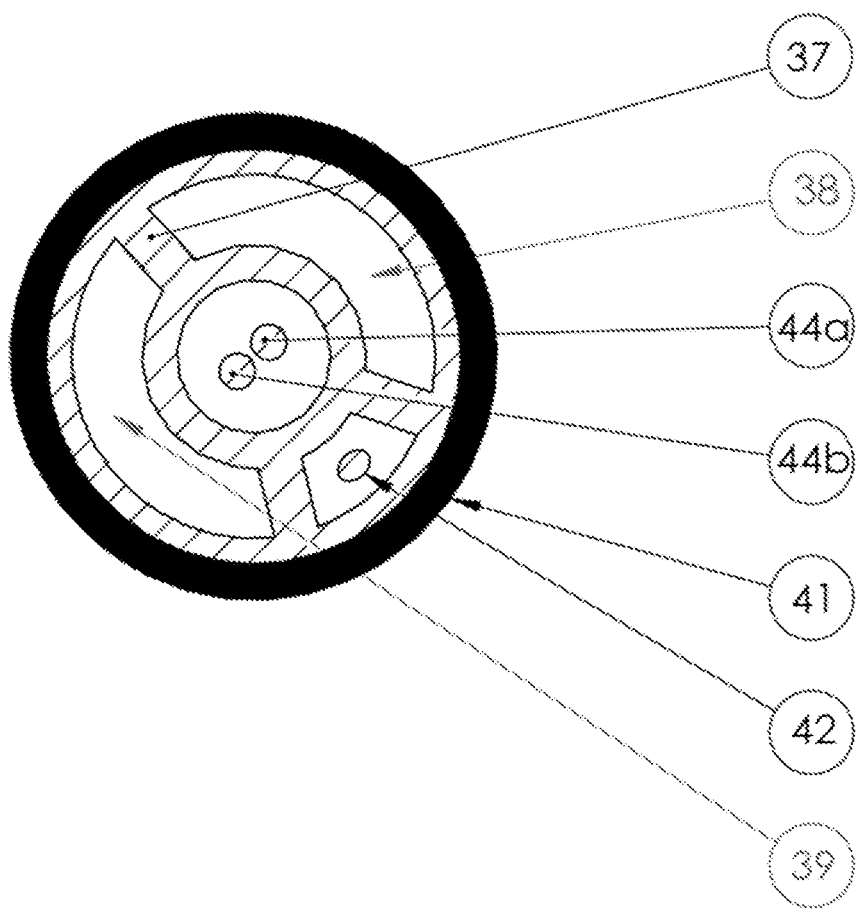
Figure 21:
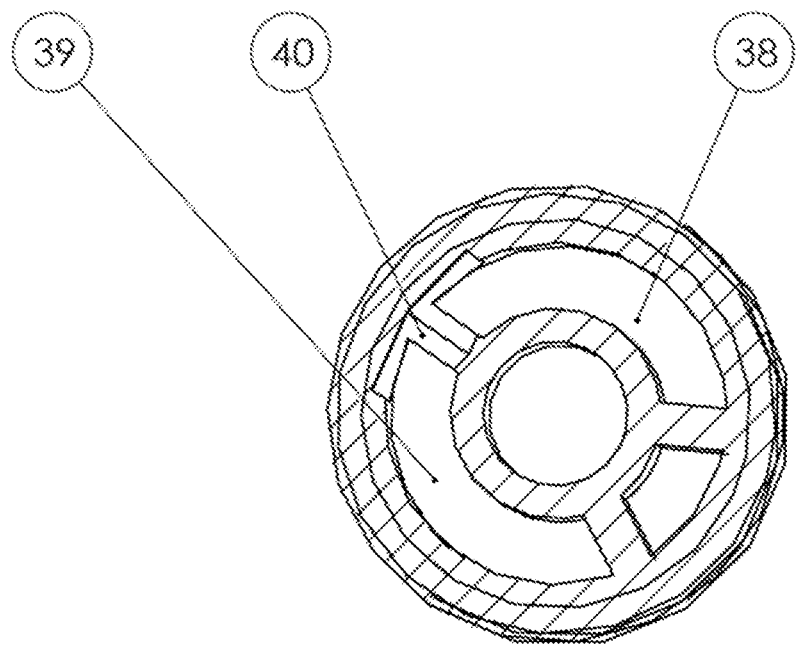

In that example the inner anodic tube is carrying on the cooling system that brings a cryogenic gas ($CO_2$, $N_2O$, or other gases) to the proximal portion of RF delivery device providing a double function of cooling and if needed a complementary cryotherapy treatment. The coaxial movement of the inner the outer tubes have, therefore, the double function of modulating at the same time the extension of the electrical field as well as the cooling/cryotherapy area as shown on FIG. 5.

This gas-based cooling system avoids the use of liquid solutions. It therefore provides a more efficient cooling system delivered with very small tubes that help designing a very thin needle or catheter bodies with a very small external diameter (for example less than 2 mm).

More specific examples are provided below:

Example A

RF and CRYO Device With Coaxial Extractable Needle and Shaft With Multi-polar Extractable Needles Made of a Memory-shape Alloy.

In this example the device provides multipolarity function between needles (>1). Needles are modified in shape after applying a telescopic action between body 7-body 8 (cathodes) and the rest of the active body (anodes).

These elements (cathodes and anodes) define the multipolarity of the said system. The electricity stream goes from proximal to distal side of the active zone of the system.

Functioning System:

After the needle puncture on the desired area, the handle allows the reverse action of 7 and 8 in order to move the active needles 2 in the desired tissue area to be treated, taking advantage of the shape memory alloy (NiTinol) of the said needles 2.

A single electrical cable connects the energy generator with the needle 7 through the handle activating the cathode part of the system. Anode function can be activated by many generator's cables that allows the activation of each needle 2 (always through the handle) in synchronized or partial mode. The number of cable varies in function of the number of active needles 2.

A second generator sends the cooling fluid through lumen 4 of the system. The fluid reaches the proximal portion of the needle 2 and it comes back to the generator through the lumen 3. The same functionality is extended to all needles 2 implemented in the device.

The combined function of RF and Cryo allows a controlled ablation of the volume to be treated avoiding negative effects such as gas production and carbonization of the tissues.

Once the treatment is completed, the needles 2 are retracted inside the major cathode 6 and it is possible to activate a Cryoablation treatment without RF in order to avoid dissemination of the cancer cells disposed along the outside surface of the needle.

The thermistors sensors are used to equalize both RF and Cryo energies in order to guarantee a stable temperature during the treatment, especially in complex parenchymal tissues such as those of liver, kidney, lungs or brain.

Example B

RF and CRYO Needle With Coaxial Extractable Needle and Multi-electrode Shaft

The device according to this example is designed with a multipolar function between the anodes, placed on 12 (12a, 12b, 12c) connected with electric cables 24 (24a, 24b, 24c) in radial position inside a shaft 23 and the cathode 18. The anode cables 24 are connected, through the handle, with the energy source generator.

Functioning System:

After the needle punctured and penetrated the area to ablate, acting on the handle the shaft 23 is retracted for the desired length in order to expose the cathode portion necessary to cover the volume of tissue to be treated.

The generator provides electrical distribution through the handle with a cable connected to 18 to activate the cathode function of the device. The anodic connections 24 are provided in the same way by cables connected to the generator. The handle carries on the control of the number of connected anodes and their charge. Multiple control functions are envisaged.

For the thermoregulation of the device a second generator provides the cooling fluid. The fluid is injected through the lumen 15 till reaching the distal tip of the needle and it return to the generator through the lumen 14.

The combined function between RF and Cryo allows ablating a controlled lesion area, in term of ablation efficacy and thermal damage avoiding tissue carbonization and gas production during the treatment.

Once the treatment is finished, the cathodic needle 18 is retracted inside the multipolar anodic shaft it is possible to activate the cryoablation treatment, without RF, in order to avoid the dissemination, in the surrounding tissues, of cancerous cells disposed along the outside surface of the needle.

The thermistor sensors, placed on the cathode tip 21a and 21b on the shaft 23, are used to equalize both RF and Cryo energies in order to guarantee a stable temperature during the treatment, especially in complex parenchymal tissues such as those of liver, kidney, lungs or brain and thyroid.

Differing from the device of example A, this device performs a thinner and ovoid ablation, reducing the extension of the treated tissue volume.

Example C

RF and CRYO Coaxial Extractable Catheter with Multi-electrode Shaft Implantable Using an Introducer Needle The system provides multi-polar anode electrodes 25 in the proximal part of the catheter, realized inside a polymeric multi-lumen shaft 35.

A number of anode cables 34 (34a, 34b, 34c) provide connections of the proximal anode electrodes, positioned in the proximal side of the device, through the handle, with the RF generator.

Similarly, to the device of example B, the electricity stream goes from the anode proximal electrodes to the cathode electrode placed in the distal tip of the catheter device.

Functioning System:

After puncturing the patient's parenchimal tissue area with a metallic introducer needle, the telescopic catheter is introduced inside it.

Once the telescopic catheter is positioned inside the introducer needle it is possible to retrieve the introducer needle without moving the telescopic catheter.

An appropriate mechanism placed on the handle allows the progressive exposition of the polymeric anodes 25 placed on the catheter 35 till reaching the desired length in order to define the tissue portion to be treated.

An electrical cable connected to the generator through the handle of the device, activates the cathode portion of the catheter. A defined number of anode electrical cables 34 (34a, 34b, 34c) link the generator through the handle and activate the anode electrodes in the proximal portion of the catheter in a synchronized way adopting different combinations.

Another generator, connected to the handle with a cable, manages the thermoregulation of the device. The cooling fluid is pumped, inside the lumen 28 of the tube 26, till the distal tip of the device. It returns then, thanks to the bypass 29, to the proximal part of tube 26 flowing out inside the lumen 27.

The combined action of RF and Cryo provides a safe and controlled ablation of the tissue to be treated that could be also pulsed RF. In this way the tissue carbonization and gas development is avoided especially when the spine ganglia are treated during a pain therapy procedure. Once the ablation treatment is finished, the cathode catheter 26 is retracted inside the multipolar anodic shaft 25. At this stage it is possible to activate the cryoablation treatment, without RF, in order to avoid the dissemination, in the surrounding tissues, of cancerous cells disposed along the outside surface of the catheter 26.

The thermistors (it's also possible to introduce one or more thermistors in the anode catheter body using other cables 32a and 32b) interact with the RF or PRF and Cryo generators in order to balance and partial both the energies. Thermistors grant a stable temperature, a safe and easy treatment during the ablation procedure. They are quite useful in case of complex parenchymal tissues such as liver, kidney, lung, brain, thyroid are treated.

Differing from the device of example A this device performs a thinner and ovoid ablation, reducing the extension of the treated tissue volume.

Example D

RF and CRYO Catheter with Coaxial, Extractable, Steerable Cathode and Multi-electrode Anode The system provides multi-polar anode electrodes 36 (36a, 36b, 36c) in the proximal part of the catheter, realized on the polymeric multi-lumen shaft 46.

Anode cables 45 (45a, 45b, 45c) provide connections between the anode electrodes, positioned in the proximal side of the device and the RF generator.

Similarly to design B, the electricity stream goes from proximal anode electrodes to the distal cathode tip electrode of the catheter.

Functioning System:

The features and functioning system of these design is similar to those of design C.

This solution is including the possibility to have a steerable and longer cathode shaft carrying on a video guide for endoluminal visualization, fiber optics to deliver laser beams, in alternative to RF or PRF energy sources, in association with Cryo.

With this technology, the steerable catheter is used to navigate inside anatomical conduits and cavities and perform ablation procedures. For example it could be applied in bronchial tree, liver's bile duct, ureters, urethra, bladder and genital cavities, oral and nasopharyngeal cavities, gastrointestinal cavities, cardiac cavities, arterial and venous blood vessels, spine's epidural accesses.

A handle performs the back movement of the polymeric anode side of the catheter 46 to the desired length in order to define, with the cathode part, the tissue portion to be treated. The same handle can manage, with two tie-rods, the steerability of the system tip.

Differently from the device of example C this device performs a thicker and elliptical ablation, reducing the radial extension of the treatment when rectilinear conditions are applied.

After the orientation of the proximal side of the system is feasible to create customize lesions during the treatment.

The distal steerable part 37 could be also obtained with a thermal shaping of the plastic polymer in order to provide customized pre-shaped curves for particular applications (e.g. prostate treatment).

Example E

Microwave Catheter and Cryogenic Cooling System

In the case of emission of microwaves for treating tumors the concept of modulated treatment area may also be used in association to a cryogenic cooling system.

This catheter has a conceptual and mechanical function overlapping and similar to that one with RF.

This catheter has a radiant field generated by an antenna 56 (coaxial cable) composed by an internal conductive element 48 and one external 50 (metallic sleeve) separated by an insulating element 49.

Figure 22:
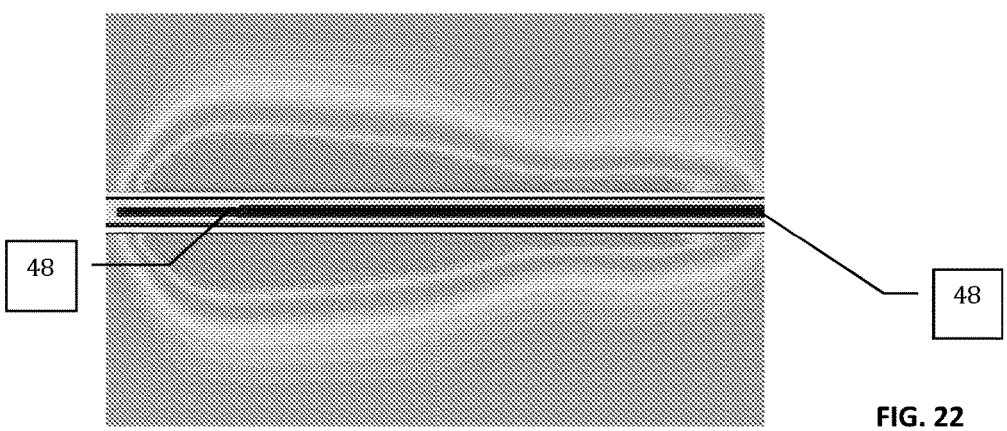
FIGS. 22 to 28: Example of a microwave ablation device according to the invention

In case the conductive element 48 would be exposed, partially removing the element 50, the shape of the microwave field could assume a diffuse pattern as that one represented in FIG. 22.

Figure 23:
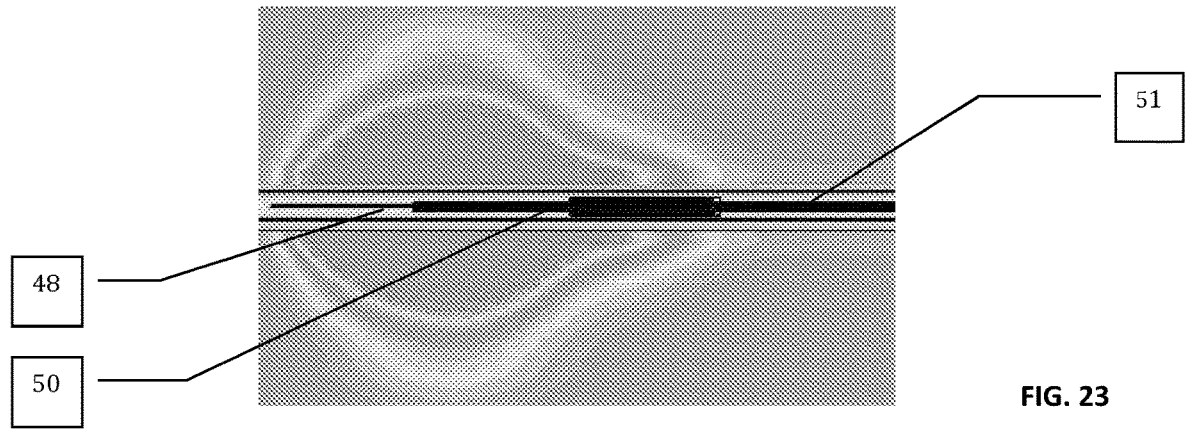

In order to further modulate the microwave field an external shield 51 is placed over the metallic sleeve 50. In this case the microwave field will concentrate more towards the tip or proximal portion of the catheter as depicted in FIG. 23.

Figure 24:
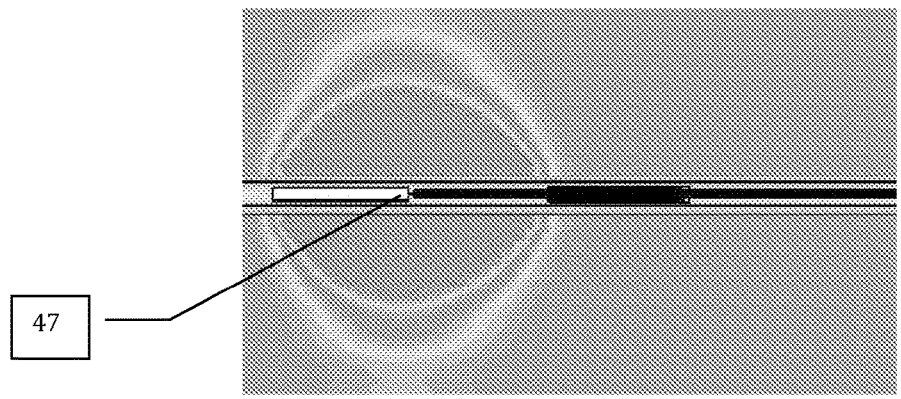

Finally mounting a metallic electrode 47 over the exposed conductive element 48 a more concentrated microwave field with spherical shape can be obtained as in FIG. 24.

This microwave catheter has the peculiarity to modulate the radiant field concentrating it in a spherical shape to maximize the efficacy of the treatment. In fact shortening the radiant field a more powerful microwave treatment can be obtained without increasing the energy erogated.

Figure 25:
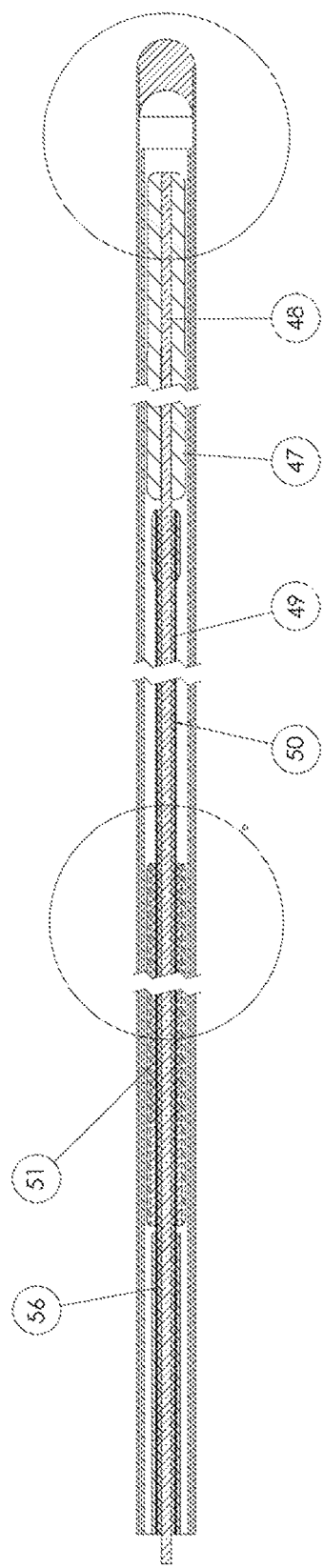
Figure 26:
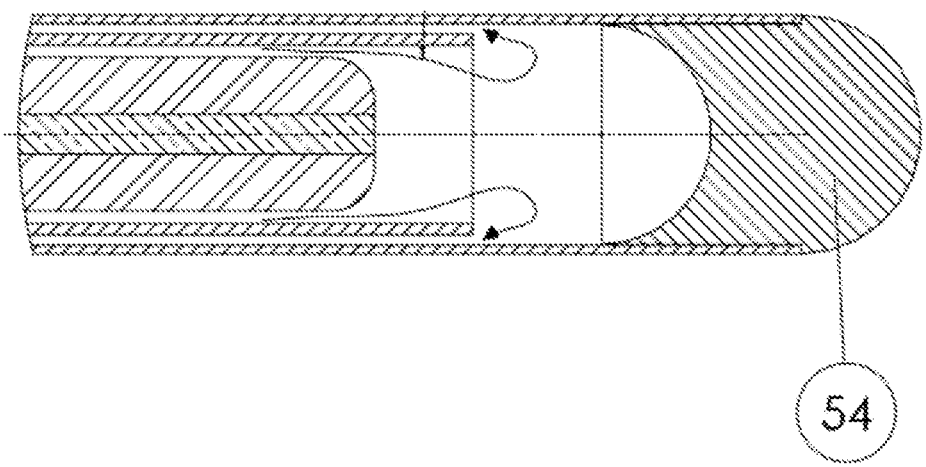

The variation of the microwave field can be obtained just modifying the relative positions of the electrode 47 and the external shield 51. A complete drawing of this microwave catheter is represented in FIG. 25.

In order to adopt this device for the treatment of tumors located in the thyroids the tissues must be well cooled down by a catheter cooling system. The device cooling is normally obtained by circulating water inside the catheter. There are several drawbacks with this cooling system. First the pressure of the circulating water is normally quite high around 6 atmospheres and the dimension of the circulating pipes inside the catheters can't be too small making this device suboptimal for small organs treatment.

The solution to this drawback can be the application of a cryogenic cooling system that will be more efficient on the tissues and smaller in diameter.

Figure 27:
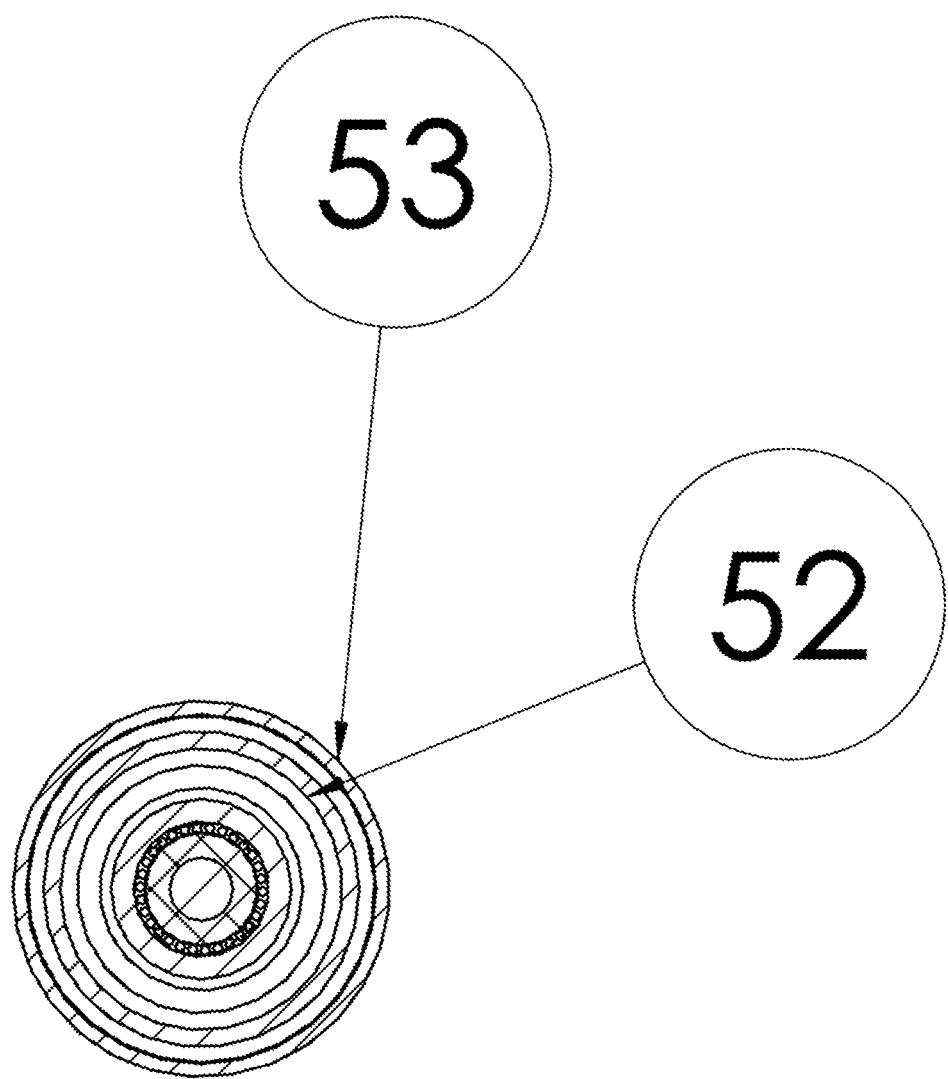
Figure 28:
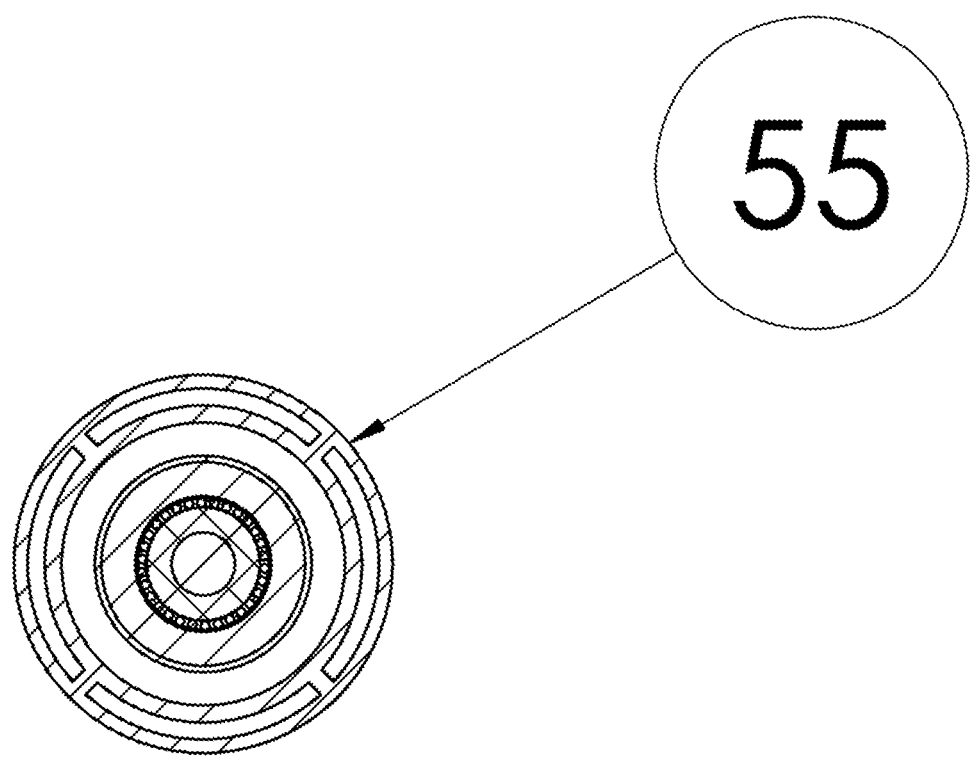

The cooling gas is circulating inside two coaxial lumens 52 and 53 or in another embodiment in a multilumen catheter 55. The cooling medium will arrive at the tip 54 of the device where in a small chamber it will reverse the flow returning back (FIG. 27 and FIG. 28).

Example F

Laser Catheter with Variable Light Emitting Field and Cryogenic Cooling System

The laser catheters are devices often used for the photonic bombardment of tumor metastases in several organs. The increased clinical use of laser fibers for these applications is indicated in association with the Magnetic Resonance or Computed Tomography imaging systems since these fibers don't alter the imaging quality.

The physical principle is based on the irradiation of the tissues with a laser beam transmitted via an optical fiber. This beam is transmitted along the fiber axis therefore a big amount of energy is released at the end of the fiber causing burning of the tissues.

The technologic evolution of the optical fibers allows obtaining a radial diffusion in specific fiber lengths. These new fibers are very useful for the treatment of tumor lesions but each lesion dimension is requiring a specific fiber length thus demanding a large catalogue of devices.

In many cases the tumor lesion is not easily measurable before the procedure therefore a radial emitting laser fiber with an adjustable emitting radial field should be recommended.

In the FIG. 29 a schematic example of a laser catheter with variable light emitting field is represented.

The laser catheter has a multilumen structure 58 that contains coaxially the laser optical fiber 57. The fiber has a portion exposed 60 that is emitting light. Mounting on the fiber itself a white moving tube 61 this portion of emitting laser fiber can be remotely modulated. The cooling system is also coaxial with cool gas entering in the section A and returning through the section B. At the proximal end of the catheter there is a tip 59. It delimitates a chamber into which the injected cool gas flow in channel A is reverted to return through the channel B (FIG. 30).

The invention is of course not limited to the examples and embodiments that are disclosed in the present document.

The invention claimed is:

1. An electromagnetic (EM) tissue ablation device for tissue ablation treatments based on endoluminal access to a treatment area, comprising:
   two coaxially arranged tubes including an external coaxial elongated tube and an internal coaxial elongated tube, the external coaxial elongated tube including a first electrode arranged at an insertion side of the external coaxial elongated tube, and the internal coaxial elongated tube including a second electrode coaxially arranged at an insertion side of the internal coaxial elongated tube, a tip of the internal coaxial elongated tube having an active needle arranged at a penetration side of the EM tissue ablation device,
   wherein the external coaxial elongated tube and the internal coaxial elongated tube are configured to be movable relative to one another along an axis of longitudinal extension of the external coaxial elongated tube, to vary a distance between the first electrode and the second electrode when viewed in a direction of the axis of longitudinal extension, the relative movement varying an extension and a shape of an EM field that is generated between the first electrode and the second electrode, and
   wherein an increased distance between the first electrode and the second electrode provides for an increased radial amplitude of the EM field and consequently an increased radial depth of the EM field in the tissue for the tissue ablation, and wherein the active needle and the tip of the internal coaxial elongated tube are configured to radially bend away from the axis of longitudinal extension of the external coaxial elongated tube when the tip of the internal coaxial elongated tube is moved away from the external coaxial elongated tube, the radially bending of the active needle permitting to move the active needle closer to the treatment area for tissue ablation during the endoluminal access by the EM tissue ablation device.

2. The device according to claim 1, further comprising:
an EM field generator operatively connected to the first and second electrodes; and
a device for causing the relative movement between the external and internal coaxial elongated tubes to vary the extension and the shape of the EM field.

3. The device according to claim 1, further comprising:
a gas-based cooling system.

4. The device according to claim 3, wherein the gas-based cooling system includes several tubes which are located within the external coaxial elongated tube.

5. The device according to claim 3, wherein the gas-based cooling system is configured to operate as a cryoablation system.

6. The device according to claim 2, wherein the EM field generator includes a RF generator, and
wherein the device is configured to vary the electrical field between the first and the second electrodes.

7. The device according to claim 6, wherein the first electrode formed by the external coaxial elongated tube has a diameter of less than 2 mm.

8. The device according to claim 6, further comprising:
conductive polymers loaded with carbon nanotubes, the conductive polymers being used for providing an electrical current to the first and second electrodes.

9. The device according to claim 2, wherein the EM field generator includes a microwave generator, and
wherein the external and internal coaxial elongated tubes are made of conductive material.

10. An electromagnetic (EM) tissue ablation device comprising:
a laser for providing tissue ablation laser light having tissue ablation energy;
two coaxially arranged tubes including an external coaxial elongated tube and an internal coaxial elongated tube;
a moving tube and an optical fiber arranged inside the internal coaxial elongated tube, the optical fiber being in operative connection with the laser for receiving the tissue ablation laser light, the moving tube configured to move relative to the optical fiber along an axis of longitudinal extension of the optical fiber; and
a tip serving as a needle arranged at a penetration side of the EM tissue ablation device,
wherein the optical fiber and the moving tube are configured to be movable relative to one another along the axis of longitudinal extension to vary a size of an exposed portion of the optical fiber at the penetration side of the EM tissue ablation device, the relative movement varying tissue ablation laser light that is radially emitted away from the optical fiber at the exposed portion.

11. The device according to claim 5, wherein the cryoablation system operates in combination with an EM field generator.

12. The device according to claim 1, further comprising:
a cooling tube arranged inside the internal coaxial elongated tube; and
a temperature sensor arranged inside a tip of the active needle,
where a cooling fluid is configured to flow between an interior of the cooling tube and an area between an exterior of the cooling tube and an interior of the internal coaxial elongated tube.

13. The device according to claim 12, further comprising:
a temperature sensor cable arranged to feed energy to the temperature sensor, arranged inside the cooling tube.

14. The device according to claim 1, wherein the external coaxial elongated tube forms a needle structure at an end facing the penetration side, and the internal coaxial elongated tube is configured to be retracted into the external coaxial elongated tube.

15. The device according to claim 10, wherein the internal and the external coaxial elongated tubes are arranged such that a cooling fluid can flow in one direction between the internal coaxial elongated tube and the moving tube, and in the other direction between the external and the internal coaxial elongated tubes.

* * * * *